(12) United States Patent
Tone et al.

(10) Patent No.: US 7,074,234 B2
(45) Date of Patent: Jul. 11, 2006

(54) STEAM GENERATOR

(75) Inventors: Hiroshi Tone, Tokyo (JP); Takayuki Kaneda, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/612,911

(22) Filed: Jul. 7, 2003

(65) Prior Publication Data
US 2004/0098072 A1  May 20, 2004

Related U.S. Application Data

(63) Continuation of application No. 09/929,000, filed on Aug. 15, 2001, now Pat. No. 6,824,557.

(30) Foreign Application Priority Data

Aug. 23, 2000 (JP) .............................. 2000-252326

(51) Int. Cl.
*A61F 7/08* (2006.01)
(52) U.S. Cl. ....................................... 607/108; 607/112
(58) Field of Classification Search ........ 607/108–112, 607/114
See application file for complete search history.

(56) References Cited

U.S. PATENT DOCUMENTS

| | | | |
|---|---|---|---|
| 4,747,841 A * | 5/1988 | Kuratomi et al. ............ 604/291 |
| 5,233,981 A * | 8/1993 | Miyashita .................... 607/114 |
| 5,342,412 A | 8/1994 | Ueki | |
| 5,425,975 A * | 6/1995 | Koiso et al. ................... 428/74 |
| 5,618,281 A * | 4/1997 | Betrabet et al. ............. 604/387 |
| 5,674,270 A | 10/1997 | Viltro et al. | |
| 5,879,378 A * | 3/1999 | Usui ........................... 607/96 |
| 6,099,556 A | 8/2000 | Usui | |
| 6,190,689 B1 * | 2/2001 | Hoffmann et al. .......... 424/448 |
| 6,198,017 B1 * | 3/2001 | Basedow et al. ............. 602/52 |
| 6,409,746 B1 * | 6/2002 | Igaki et al. ................. 607/109 |
| 6,669,953 B1 * | 12/2003 | Kamiyama .................. 424/449 |
| 6,841,716 B1 * | 1/2005 | Tsutsumi ..................... 602/57 |

FOREIGN PATENT DOCUMENTS

| | | |
|---|---|---|
| EP | 1 090 614 | 4/2001 |
| GB | 2 312 846 | 11/1997 |
| JP | 1-250252 | 10/1989 |
| JP | 02131760 A | 5/1990 |
| JP | 7-233050 | 9/1995 |
| JP | 8-112303 | 5/1996 |
| JP | 9-12449 | 1/1997 |
| JP | 9-87171 | 3/1997 |
| WO | WO96/08245 | 3/1996 |
| WO | WO 99/51174 | 10/1999 |

* cited by examiner

*Primary Examiner*—Roy D. Gibson
*Assistant Examiner*—Aaron Roane
(74) *Attorney, Agent, or Firm*—Oblon, Spivak, McClelland, Maier & Neustadt, P.C.

(57) ABSTRACT

There is provided a steam generator for a sustained supply, in a simple and easy way and without displacement, of steam that is as safe as in a steamed towel to the body skin or mucosa. The steam generator has a steam generation portion composed of a steam-generating composition containing a metal powder, a salt, and water, and an adhesive layer on the surface which is to be applied to the skin or mucosa. The steam-generating composition discharges steam as the metal powder is oxidized. In the steam generation portion, the steam-generating composition is held or sandwiched in a support so as to inhibit the movement of the steam-generating composition inside the steam generation portion, and the steam generation portion itself is formed into a sheet.

16 Claims, 3 Drawing Sheets

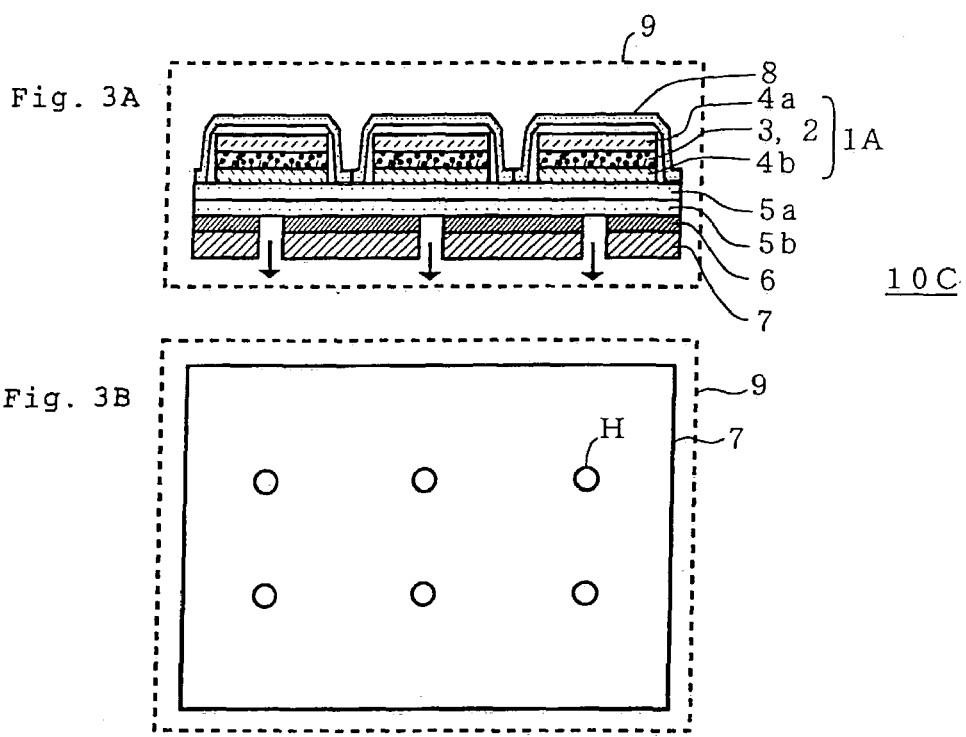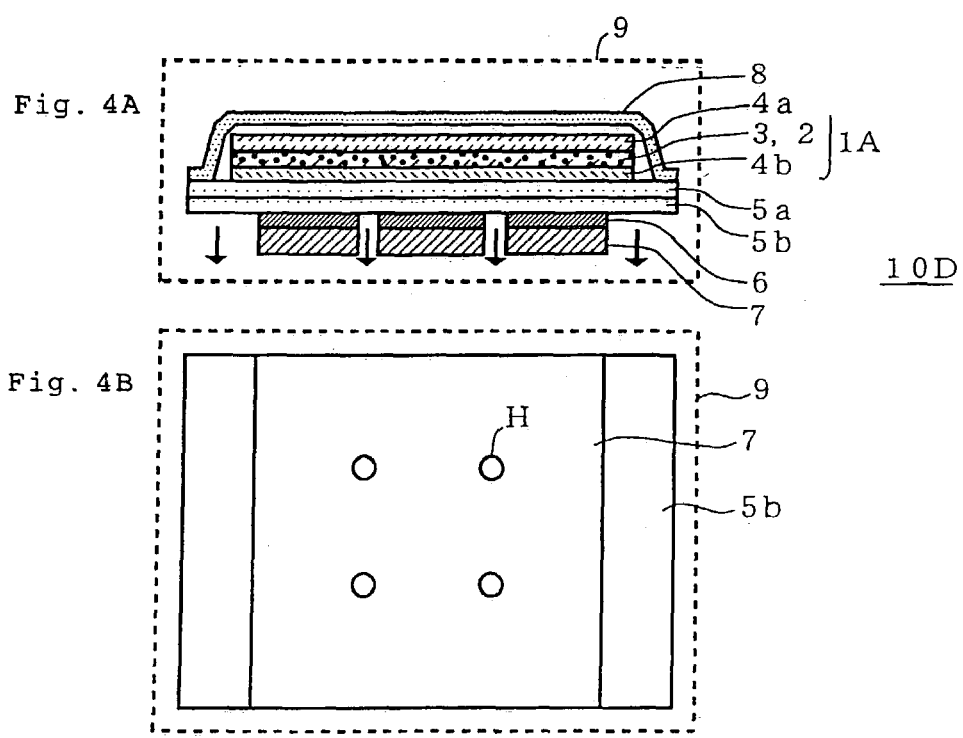

STEAM GENERATOR

STATEMENT OF RELATED APPLICATIONS

The patent application is a continuation of U.S. patent application Ser. No. 09/929,000 filed 08/15/2001 now issued as U.S. Pat. No. 6,824,557.

BACKGROUND OF THE INVENTION

1. Field of the Invention

The present invention relates to a steam generator moisturizing the skin of body parts such as the scalp, shoulders, neck, face, waste, buttocks, feet, hands, arms etc., or mucosa of eyes, nose, throat etc., by supplying steam thereto, and more particularly to a steam generator which makes it possible to cause the effective transepidermal absorption of a cosmetic or pharmaceutical component by means of steam and heat.

2. Description of the Related Art

Steam beautification devices, steamed towels and the like have been used to supply the appropriately heated steam to the skin, thereby enhancing circulation of blood in the skin as well as maintaining the skin in a desired moisturized state or bringing it into such state.

However, the steam beautification devices or steamed towels cannot be used at all times in any places. Moreover, the steam beautification devices are difficult to use on the body parts other than the face, and the problem associated with the steamed towels is that too short is a retention time in which a sufficient amount of steam can be supplied.

SUMMARY OF THE INVENTION

It is an object of the present invention to resolve the above-described problems inherent to the prior art technology, to enable a sustained supply of safe steam, similar to that from steamed towels, to the skin or mucosa in a simple and easy way with a pleasant utilization feeling, and also to supply a cosmetic or pharmaceutical component simultaneously with the steam to the skin or mucosa, provide for effective permeation of the cosmetic or pharmaceutical component through the skin or mucosa, and greatly enhance the utilization efficiency thereof.

In order to attain the aforesaid object, the present invention provides a steam generator applicable to the skin or mucosa, which has a steam generation portion comprising a steam-generating composition containing a metal powder, a salt, and water and discharging steam as the metal powder is oxidized, wherein the steam-generating composition is supported on or held in a support so as to inhibit the movement of the steam-generating composition in the steam generation portion, the steam generation portion is formed into a sheet, and an adhesive layer is provided on the surface of the steam generator which is applied to the skin or mucosa.

In the especially preferred embodiment of the steam generator, a cosmetic or pharmaceutical component is contained in the adhesive layer.

The steam generator in accordance with the present invention is applied to the skin or mucosa. The application of the steam generator to the skin or mucosa as referred to herein, for example, means that the steam generator is brought in contact with the skin or mucosa by sticking thereto or other measures.

Further, in accordance with the present invention, the steam discharged from the steam generator includes both the steam resulting from the evaporation of water and formation of a gas phase and the steam having fine water droplets formed by the condensation of the gas.

In the steam generator in accordance with the present invention, a steam-generating composition containing a metal powder, a salt, and water and discharging steam as the metal powder is oxidized is used in the steam generation portion. Therefore, moisture and heat can be supplied to the skin or mucosa in any part of the body in a simple and easy way and at any time.

Further, since an adhesive layer is provided on the surface of the steam generator which is applied to the skin or mucosa, the steam generator can be very easily stuck to the desired part on the skin or mucosa and no special holder is required.

In particular, if a cosmetic or pharmaceutical component is introduced into the adhesive layer, since the steam brings the skin or mucosa and the adhesive layer in a hot and moist state, the permeation rate of the cosmetic or pharmaceutical component into the skin or mucosa is increased and the utilization efficiency thereof can be increased.

Further, in the steam generator in accordance with the present invention, the steam-generating composition is held or sandwiched in the support so as to inhibit the movement of the steam-generating composition in the steam generation portion. Therefore, the displacement of the steam-generating composition during maintenance or utilization of the steam generator and the formation of unevenness in the steam generation zone can be prevented and a problem associated with the unpleasant utilization feeling created by dangling lump-like portions of the steam-generating composition can be resolved. Moreover, because the steam generation portion in the steam generator in accordance with the present invention is formed into a sheet, it can be used with good sensation caused by sticking.

BRIEF DESCRIPTION OF THE DRAWINGS

FIGS. 3A and 3B are respectively a cross-sectional view and a plan view of the steam generator;

FIGS. 4A and 4B are respectively a cross-sectional view and a plan view of the steam generator;

DETAILED DESCRIPTION OF THE INVENTION

Figure 1A:
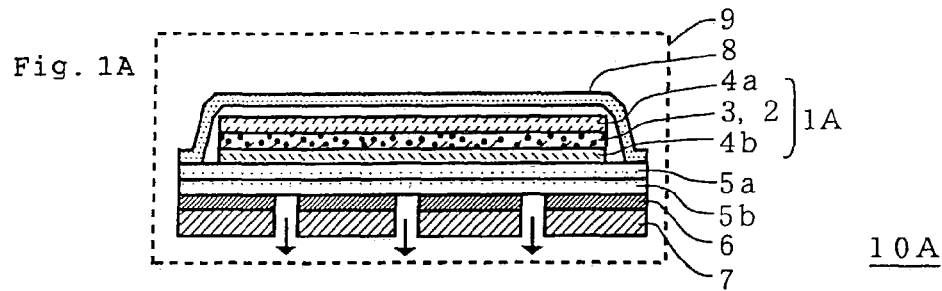
FIGS. 1A and 1B are respectively a cross-sectional view and a plan view of the steam generator.

The present invention will be described below in greater detail with reference to the drawings. In the drawings, same or identical structural elements are denoted with the same symbols.

Figure 1B:
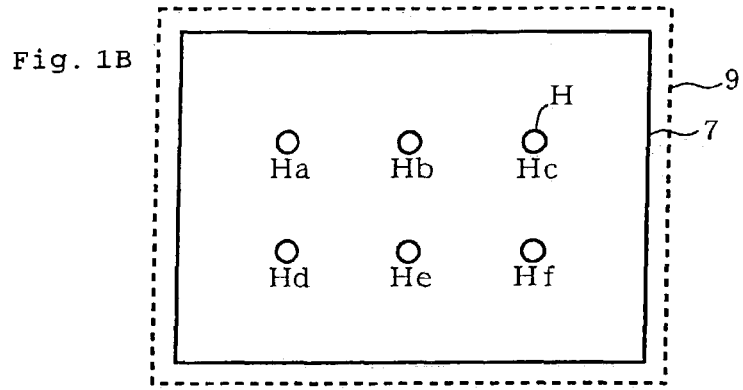

FIGS. 1A and 1B are respectively a cross-sectional view and a plan view of a steam generator 10A which is an example of the present invention.

Steam generator 10A is constituted by a steam generation portion 1A formed into a sheet, moisture-permeable sheets 5a, 5b successively laminated on the steam generating surface of steam generation portion 1A, a moisture-impermeable sheet 6, an adhesive layer 7, a gas-permeable sheet 8 laminated on the other surface of steam generation portion 1A, and a sealing bag 9 enclosing and sealing all of the above components. When steam generator 10A is used, sealing bag 9 is ruptured, the content thereof is removed therefrom, and adhesive layer 7 is stuck to the skin or mucosa. Further, openings H guiding the steam emitted from steam generation portion 1A to the skin or mucosa are provided in moisture-impermeable sheet 6 and adhesive layer 7 of steam generator 10A.

Steam generation portion 1A is composed of a steam-generating composition 2 maintained in a supported condition on a support. A composition containing a metal powder (iron, aluminum, zinc, copper and the like), a salt (sodium chloride, potassium chloride, calcium chloride, magnesium chloride and the like), and water, generating heat by oxidation of the metal powder as expressed by the following formula:

$$Fe + (3/4)O_2 + (3/2)H_2O \rightarrow Fe(OH)_3 + 96 \text{ kcal},$$

and emitting the water present in the system as steam is used as the steam-generating composition 2. From the standpoint of cost efficiency, reactivity, and safety, it is preferred that an iron powder be used as the metal powder. Further, various components such as water-retaining agents (vermiculite, calcium silicate, silica gel, silica-based porous substances, alumina, pulp, wood flour, water-absorbing polymer and the like) or reaction promoters (active carbon, carbon black, graphite and the like) can be incorporated in the steam-generating composition.

Steam generation portion 1A has a sheet-like structure in which steam-generating composition 2 is dispersed and retained inside the pores of a nonwoven fabric 3 having a multiplicity of pores, and nonwoven fabrics 4a, 4b are placed on both surfaces thereof so as to inhibit the movement and prevent the displacement of steam-generating composition 2 in steam generation portion 1A. Such formation of steam generation portion 1A into a sheet can prevent the displacement of the steam generation zone when steam generator 10A is used and can also improve the sensation caused by sticking.

No limitation is placed on fiber materials in nonwoven fabric 3 having a multiplicity of pores, but because of high water-retention ability thereof, it is preferred that cotton, pulp and the like be used. Furthermore, to provide the nonwoven fabric 3 with capability to retain a sufficient amount of the steam-generating composition, the nonwoven fabric 3 preferably has a porosity of no less than 60% and a basic weight of 10–300 g/m².

On the other hand, nonwoven fabrics 4a, 4b are provided to prevent leakage of steam-generating composition 2 retained in the pores of the above-described nonwoven fabric 3. Nonwoven fabrics which are more dense than nonwoven fabric 3 and, for example, have a basic weight of 10–150 g/m² are preferably used as the nonwoven fabrics 4a, 4b.

A specific method for the manufacture of steam generation portion 1A, for example, comprises the steps of laminating nonwoven fabric 3 having a multiplicity of pores with comparatively dense nonwoven fabric 4a by using an adhesive, scattering a powdered component of the constituents of steam-generating composition 2 over the upper surface of nonwoven fabric 3, and applying vibrations or using vacuum suction so that the steam-generating composition 2 is retained in the pores of nonwoven fabric at a ratio of 500–8000 g/m². Then, nonwoven fabric 4b is placed on the scattering surface and the laminate is thermally compressed at a temperature of 70–250° C. under a linear pressure of 0.5–100 kg/cm, and processed into a sheet-like product with a thickness of 0.5–20 mm, preferably, 1–6 mm. Steam generation portion 1A is then obtained by impregnating the sheet-like product with an aqueous solution containing a salt among the constituents of steam-generating composition 2.

The formulation of steam-generating composition 2 used in steam generator 11A has been employed as a heater generally termed as a chemical body warmer. However, since the conventional chemical body warmers have been basically constructed as heating tools, they have been designed so as to have a proper gas permeability and to prevent the escape of water necessary for the reaction from the heat generator. For this purpose, the bags containing the heater of the chemical body warmer are not purposely constructed of materials that are permeable to moisture, even though they are permeable to gas. For example, in Japanese Patent Application Laid-open No. H1-250252, a sheet was used which had a moisture permeability of 10–400 g/m²·24 h, as determined by an ASTM method (E-96-80D method).

By contrast, in steam generator 10A, the steam-generating composition 2 is positively used as a steam generation source, this utilization mode thereof being markedly different from that of a similar composition in the conventional chemical body warmers. For that purpose, the layer of steam generation portion 1A at the skin or mucosa side is formed from a moisture-permeable material (including moisture-impermeable materials that as a whole are rendered moisture permeable, for example, by forming holes therein), preferably, from a moisture-permeable material with a moisture permeability of no less than 500 g/m²·24 h, more preferably, no less than 800 g/m²·24 h, still more preferably, 1000–3000 g/m²·24 h, and even more preferably, 1400–2800 g/m²·24 h. As a result, the amount of steam discharged from the surface of steam generator 10A which is applied to the skin or mucosa is no less than 0.002 mg/cm²·min, preferably, no less than 0.01 mg/cm²·min, and still more preferably, no less than 0.5 mg/cm²·min. Here, the steam discharge portion denotes a portion from which the steam is directly emitted to the skin or mucosa, for example, the openings H of steam generator 10A in FIGS. 1A and 1B.

The amount of steam discharged from the surface of steam generator 10A which is applied to the skin or mucosa is determined by the weight measurement method comprising the steps of removing the steam generator 10A from an atmosphere-shielding container under a room temperature environment (20° C., 65% RH), immediately placing it on a top-pan balance capable of weighing to the nearest 1 mg, and then conducting measurements for 15 min. In this method, the amount of steam is calculated by the following Formula 1 in which $Wt_0$ (g) stands for the weight at the instant the measurement is started, $Wt_{15}$(g) stands for the weight after 15 min, and S (cm²) stands for the area of the portion of the steam generator surface which is applied to the skin or mucosa.

$$\text{Amount of discharged steam } (mg/cm^2 \cdot min) = (Wt_0 - Wt_{15}) \cdot 1000/155 \qquad (1)$$

Furthermore, the amount of steam discharged from the steam discharge portion of steam generator 10A is a numerical value (mg/cm²·min) of the amount of discharged steam determined by removing steam generator 10A from an atmosphere-shielding container under a room temperature environment (20° C., 65% RH), immediately placing it in a transepidermal water evaporation measurement device (Evaporimeter; manufactured by ServoMed Co.), measuring humidity in the steam discharge portion for 60 min, and conducting calculations from the maximum value of humidity within 60 min.

In accordance with the present invention, it is preferred that either the amount of discharged steam determined by the weight measurement method or the amount of discharged steam determined with the transepidermal water evaporation measurement device be within the aforesaid range.

Furthermore, when adhesive layer 7 of steam generator 10A comprises a water-soluble substrate, the adhesive layer 7 essentially contains a large amount of water and discharges steam by itself. For that reason, when the amount of steam discharged from steam generator 10A is measured merely by the above-described weight measurement method or with the transepidermal water evaporation measurement device, it is impossible to determine whether the measured amount of steam has been contained essentially in the adhesive layer 7 or in steam-generating composition 2 and the measured amount of steam cannot serve as the indicator of steam discharge ability of steam generation portion 1A. Accordingly, when adhesive layer 7 comprises a water-soluble substrate, it is preferred that the amount of discharged steam is measured upon removal of adhesive layer 7 from steam generator 10A.

Examples of materials for moisture-permeable sheets 5a, 5b in steam generator 11A include woven fabrics, nonwoven fabrics, paper, synthetic paper and the like obtained from fibers of one type or a mixture of fibers of at least two types selected from synthetic fibers such as nylon, vinylon, polyester, rayon, acetate, acryl, polyethylene, polypropylene, poly(vinyl chloride) and the like, and natural fibers such as pulp, cotton, jute, silk, animal hair and the like. Furthermore, examples of materials suitable for moisture-impermeable sheet 6 having openings H provided therein include gas-impermeable films or sheets composed of polyethylene, polypropylene, polyamide, polyester, poly(vinyl chloride), poly(vinylidene chloride), polyurethane, polystyrene, saponified ethylene-vinyl acetate copolymer, ethylene-vinyl acetate copolymer, natural rubber, regenerated rubber, synthetic rubber and the like, these films or sheets having holes provided therein.

On the other hand, gas-permeable sheet 8 laminated on the side of steam generation portion 1A that is opposite to the surface thereof which is applied to the skin or mucosa is preferably formed from a material with moisture permeability lower than that of moisture-permeable sheets 5a, 5b on the surface which is applied to the skin or mucosa and moisture-impermeable sheet 6 having openings H provided therein. For example, it is preferably formed from a sheet with a comparatively low moisture permeability (for example, Japanese Patent Application Laid-open No. H1-250252) that is generally used in chemical body warmers. As a result, steam from steam generation portion 1A can be effectively discharged toward the skin or mucosa. Gas-permeable sheet 8 is made gas permeable to supply oxygen to steam-generating composition 2 therethrough. If the area of openings H or the mounting areas of moisture-impermeable sheet 6 and of adhesive sheet 7 were adjusted so as to supply the sufficient amount of oxygen from the surface of application to the skin or mucosa to steam-generating composition 2, then a gas-impermeable sheet may be used instead of gas-permeable sheet 8.

In the process for the manufacture of steam generator 10A, the moisture-permeable sheet 5a and gas-permeable sheet 8 may be individually laminated on steam generation portion 1A, but the steam generation portion 1A may also be enclosed in a bag having one surface thereof composed of moisture-permeable sheet 5a and the other surface composed of gas-permeable sheet 8.

Moisture-permeable sheet 5b is preferably provided with a function of a temperature-adjusting material which controls with good stability and reliability the temperature of steam discharged from the surface of steam generator 10A that is applied to the skin or mucosa to no more than 50° C., preferably, no more than 45° C., even more preferably, 38° C.–42° C. Accordingly, it is preferred that a nonwoven fabric or synthetic paper, even those selected from the above-described moisture-permeable sheets, be used as moisture-permeable sheet 5b.

When the steam temperature is controlled in accordance with the present invention, the temperature measurement can be conducted by removing the steam generator from an atmosphere-shielding container under a room temperature environment (20° C., 65% RH), placing the steam generator, with the steam generation surface facing down, on a foamed styrol base, setting the temperature detection unit of a temperature meter (Thermorecorder RT-10; manufactured by Tabai Espec Corp.) on the steam generation surface thereof so as to apply no weight to the steam generator, and measuring the temperature between the steam generation surface and foamed styrol base. When the steam generator has openings H on the surface which is applied to the skin or mucosa, as in steam generator 11A shown in FIGS. 1A and 1B, the temperature detector is set in the openings H.

When moisture-permeable sheet 5b is composed of a nonwoven fabric or synthetic paper, their specific weight, thickness and the like are determined appropriately according to the desired amount of steam discharged from the surface of steam generator 10A because the nonwoven fabric or synthetic paper exhibits resistance to the passage of steam generated by steam generation portion 1A. Further, if the steam temperature immediately after the discharge from steam generation portion 1A is no more than 50° C., preferably, no more than 45° C., then the need for nonwoven fabric or synthetic paper is obviated. The thickness of adhesive layer 7 may be increased to control the temperature of steam discharged from the surface of steam generator 10A that is applied to the skin or mucosa to no more than 50° C.

Adhesive layer 7 is intentionally installed in the surface of steam generator 10A that is applied to the skin or mucosa rather than on the outer edge of the application surface. As a result, steam generator 10A can be attached to the desired application portion in a much more simple and reliable manner than when adhesive layer 7 is simply present on the outer edge of the application surface.

If necessary, a cosmetic or pharmaceutical component can be incorporated in adhesive layer 7. In such case, the cosmetic or pharmaceutical component can exert effect on the skin or mucosa, which was heated and moisturized by steam, from the adhesive layer 7 that is in a hot and moist state. Therefore, the permeation rate of the cosmetic or pharmaceutical component through the skin or mucosa is increased and the utilization efficiency thereof is increased. The temperature and moisture effect in such steam generator 10A is much higher than that obtained when an adhesive layer having a cosmetic or pharmaceutical component incorporated therein was simply attached to a conventional chemical body warmer (that is, when in a chemical body warmer with an adhesive layer backing, the steam was not specially supplied by heating the adhesive layer, and the skin or adhesive layer was moisturized by sweat from the skin), and the cosmetic or pharmaceutical component are effectively caused to permeate through the skin or mucosa.

Further, a plurality of round openings H (Ha, Hb, Hc, Hd, He, Hf) are provided in adhesive layer 7. As a result, the steam discharged from steam generation portion 1A can be effectively guided to the skin or mucosa exclusively through openings H, as shown by an arrow. From the standpoint of supplying a sufficient amount of steam and a cosmetic or pharmaceutical component to the skin or mucosa, the surface area ratio of openings H is preferably 0.1–50%, even more preferably, 0.5–30% of the entire surface over which the steam generator 10A is applied to the skin or mucosa.

No specific limitation is placed on the material constituting the adhesive layer 7, and adhesives composed of water-soluble or water-insoluble substrate can be used. For example, an adhesive substrate composed of an aqueous gel obtained by using a crosslinking agent of a water-soluble polymer (Japanese Patent Application Laid-open No. H9-87171, paragraphs [0011]~[0018]), aqueous adhesives, acrylic adhesives, rubber-based adhesives, silicone resin adhesives, adhesives based on natural polymers, cellulose polymers, starch polymers, synthetic polymers and the like (Japanese Patent Applications Laid-open No. H9-12449, paragraphs [0012]~[0018], and No. 7-233050, paragraphs [0009]~[0024]), WO96/08245, page 5, line 18 to page 6, line 2) can be used.

Furthermore, examples of cosmetic or pharmaceutical components incorporated in adhesive layer 7 include blood circulation enhancers such as acidic mucopolysaccharides, chamomile, horse chestnut, ginkgo, hamamelis extract, Vitamin E, nicotinic acid derivatives, alkaloid compounds and the like; swelling-reducing agents such as horse chestnut, flavone derivatives, naphthalenesulfonic acid derivatives, anthocyanins, Vitamin P, *Calendula officinalis*, concholytic acid, silanol, Terminalia, Visnaga, Majus and the like; slimming agents such as aminophylline, tea extract, caffeine, xanthine derivatives, inositol, dextransulfuric acid derivatives, horse chestnut, aescin, anthocyanidin, organoiodine compounds, *Hypericum erectum, Spiraea japonica, Equisetum arvense, Rosmarinus officinalis*, gingsen, *Hedera rhombea*, thiomucase, hyaluronidase and the like; painkillers such as indometacin, diclofenac, dl-camphor, flurbiprofen, ketoprofen, cayenne pepper extract, piroxicam, felbinac, methyl salicylate, glycol salicylate and the like; moisture-retaining agents, for example, polyols such as glycerin, ceramides, collagens, and the like; peeling agents composed of protease such as papain; depilating agents such as calcium thioglycolate; and autonomic regulating agents such as γ-oryzanol.

When protease is used as a peeling agent in adhesive layer 7, the protease can be immobilized by the ordinary method employed in preparation of immobilized enzymes. The catalytic activity of the protease thus immobilized is increased by the steam and heat supplied from steam-generating composition 2. Therefore, an old horny layer present on elbows, knees, heels and the like can be effectively removed.

Incorporating cosmetic or pharmaceutical components in adhesive layer 7, as described above, can increase the utilization effect thereof. In particular, if a depilating agent is used, the steam supplied from steam-generating composition 2 causes swelling and softening of the area surrounding hair root. As a result, pain associated with depilating can be greatly relieved in comparison with the conventional methods for using the depilating agents and an excellent depilating effect can be obtained.

Figure 2A:
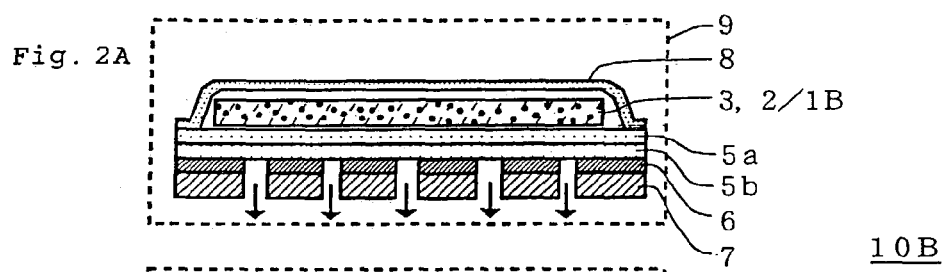
FIGS. 2A, 2B, and 2C are respectively a cross-sectional view and a plan view of the steam generator and a schematic view of the steam generation portion.
Figure 2B:
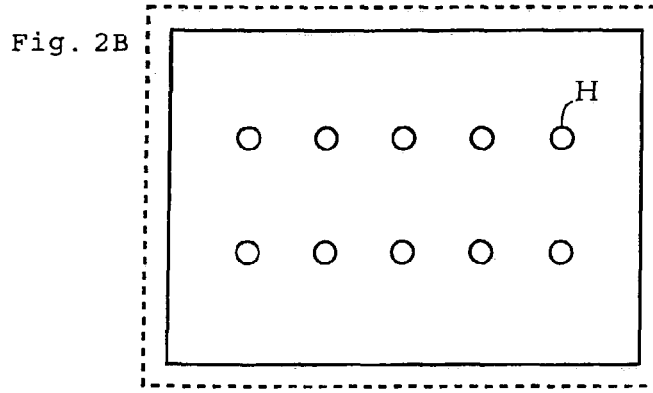

FIGS. 2A and 2B are respectively a cross sectional view and a plan view of steam generator 10B which is another embodiment of the present invention.

Common to the steam generator 10B and steam generator 10A shown in FIGS. 1A and 1B is that steam generation portion 1B composed of nonwoven fabric 3 having a plurality of pores in which the steam-generating composition 2 is dispersed and retained, but steam generator 10B differs from steam generator 10A in that both surfaces of nonwoven fabric 3 where steam-generating composition 2 was dispersed and retained is not held between other nonwoven fabrics and in that the number of openings provided in gas-permeable sheet 6 and adhesive layer 7 is large.

Figure 2C:
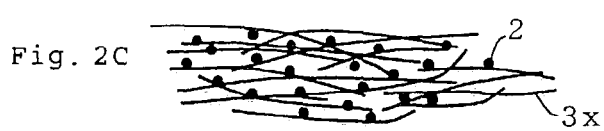

Steam generation portion 1B can be obtained by scattering a metal powder, as a component of steam-generating composition 2, and applying vibrations or using vacuum suction to retain the steam-generating composition in the pores of nonwoven fabric 3, and then impregnating with a suspension composed of other components of steam-generating composition 2. FIG. 2C is a schematic diagram of steam generation portion 1B thus obtained, this figure illustrating a state in which steam-generating composition 2 is retained in the pores between fibers 3x of nonwoven fabric.

A steam generator 10C shown in FIGS. 3A and 3B represents an embodiment in which, by contrast with steam generator 10A shown in FIGS. 1A and 1B, the steam generation portion 1A and gas-permeable sheet 8 are divided into a plurality of small units and openings H are provided over each steam generation portion 1A.

Providing a plurality of steam generation portions 1A in one steam generator 10C in the above-described manner can increase the flexibility of steam generator 10C and weaken a feeling of physical disorder when the steam generator is applied to the body. Further, when a plurality of steam generation portions 1A are provided, they may be brought in contact to each other as shown in FIGS. 3A and 3B, or bonded, for example, by thermal fusion, or they may be separate from each other.

In a steam generator 11D shown in FIGS. 4A and 4B, by contrast with steam generator 10A shown in FIGS. 1A and 1B, the adhesive layer 7 is not provided on the peripheral edge of the surface over which the steam generator 10D is applied to the skin or mucosa and the entire steam discharged from steam generation portion 1A is supplied to the skin or mucosa from the peripheral edge of the surface over which the steam generator 10D is applied to the skin or mucosa and from the openings H provided in adhesive layer 7.

Figure 5A:
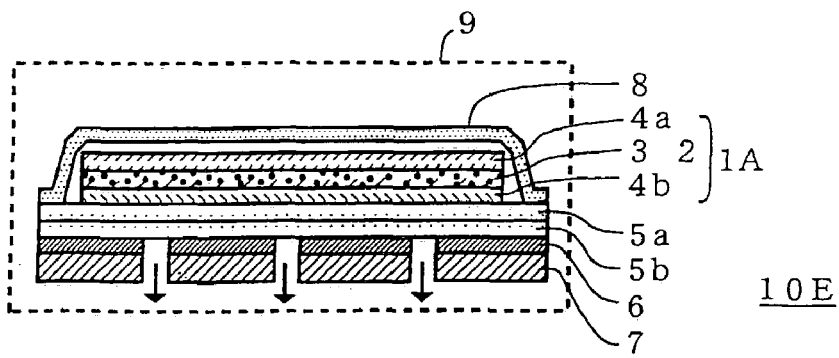
FIG. 5 is a cross-sectional view of the steam generator.
Figure 5B:
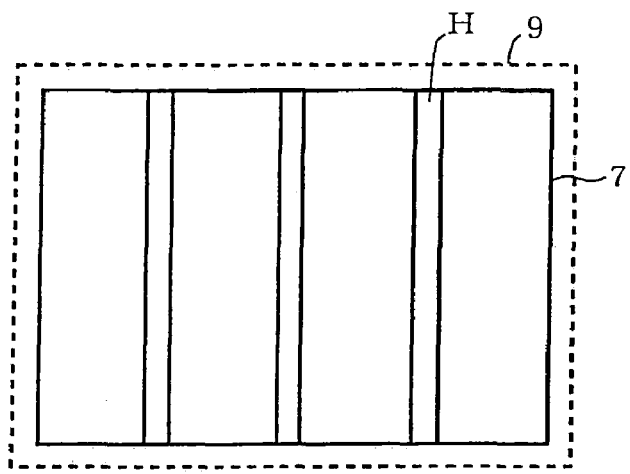

A steam generator 10E shown in FIGS. 5A and 5B differs from steam generator 10A shown in FIGS. 1A and 1B in that the openings H provided in adhesive layer 7 have a bandlike shape rather than round shape.

Thus, the present invention places no limitation on the shape of openings H that guide the steam discharged from steam generation portion 1A to the skin or mucosa through the adhesive layer 7. Moreover, no limitation is placed on the formation position of adhesive layer 7 on the surface of steam generator which is applied to the skin or mucosa or on the surface area thereof. However, if adhesive layer 7 is formed over the entire application surface, the amount of steam supplied to the skin or mucosa is reduced excessively. For this reason, the formation area of adhesive layer 7 is preferably 50%~99.9%, even more preferably, 70%~99.5% of the entire surface over which the steam generator is applied to the skin or mucosa.

Figure 6:
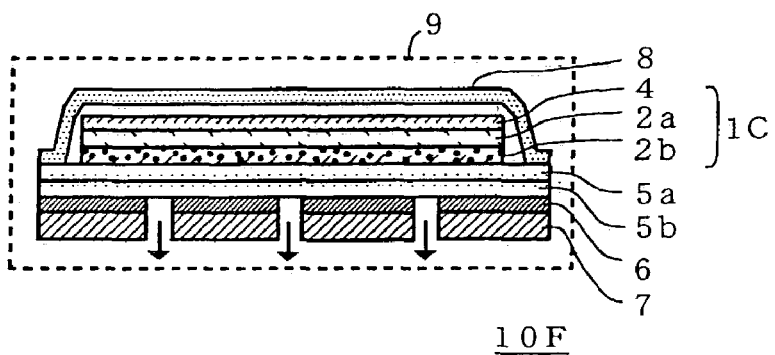
FIG. 6 is a cross-sectional view of the steam generator.

In a steam generator 10F shown in FIG. 6, a laminated material composed of a laminate of a coating layer 2a of a viscous liquid or liquid prepared by mixing a salt, water, and, if necessary, a water-retaining agent, as components of the steam-generating composition, and a powder layer 2b containing a metal power and laminated thereon is provided on nonwoven fabric 4 serving as a support, this laminated material acting as a steam generation portion 1C in place of steam generation portion 1A of steam generator 10A shown in FIGS. 1A and 1B.

Figure 7:
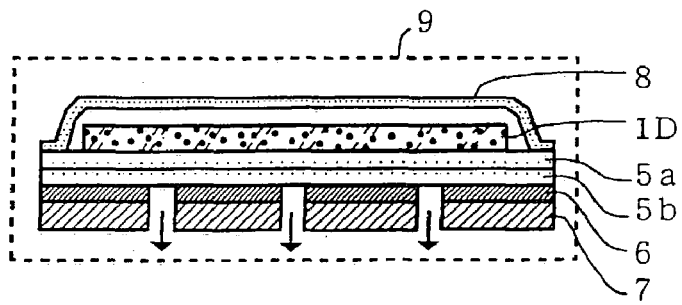
FIG. 7 is a cross-sectional view of the steam generator.

In a steam generator 10G shown in FIG. 7, a thin sheet formed from the steam-generating composition and a fibrous substance is used as a steam generation portion 1D in place of steam generation portion 1A of steam generator 10A shown in FIGS. 1A and 1B. Various natural or synthetic fibers can be used as the fibrous substance, but from the standpoint of gas permeability and cost, pulp is especially preferred. The thin sheet is preferably formed to have a water content of 5–60 wt. %, a metal powder ratio of 5–70 wt. %, and a thickness of 0.5–20 mm, in particular, 1–6 mm.

Thus, in accordance with the present invention, the steam generation portion can be in a variety of forms, provided that the steam-generating composition is supported on or held in a support so as to inhibit the movement of the steam-generating composition in the steam generation portion, and the steam generation portion is formed into a sheet.

For example, in steam generator 10A shown in FIGS. 1A and 1B, at least one of the following sheets: (1) cloth, (2) paper-like product such as paper, synthetic paper and the like, (3) porous films or porous sheets formed from plastics, natural rubbers, regenerated rubbers or synthetic rubbers, (4) foamed plastics such as perforated urethane foam and the like, and (5) metal foils such as perforated aluminum foil, can be used in place of the nonwoven fabric as the moisture-permeable sheet 5b serving to control the temperature of steam supplied to the skin or mucosa. Those temperature-adjusting materials may be used individually or as a laminate of a plurality of structural components. The lamination method and the way they are combined in case of lamination are appropriately determined so as to supply the preset amount of steam with preset temperature to the skin or mucosa.

Furthermore, the particle size and specific surface area of the metal powder, such as iron powder, used in steam-generating composition 2 and the amount of the metal powder present on an area of 1 cm$^2$ over which the steam generator is applied to the skin or mucosa may be appropriately adjusted to control the temperature of steam supplied to the skin or mucosa.

A layer having a cosmetic or pharmaceutical component supported therein may be separately provided between the steam generation portion 2 and adhesive layer 7, without incorporating the component into adhesive layer 7.

EXAMPLES

Example 1

Steam generator 10A of the embodiment shown in FIGS. 1A and 1B was prepared in the following manner.

First, an iron powder (RKH; manufactured by Dowa Iron Powder Co., Ltd.) 50 wt. %, table salt 3 wt. %, water 27 wt. %, active carbon 5 wt. %, and vermiculite (manufactured by Shinsei Micron Co., Ltd.) 15 wt. % were mixed to give 20 g of steam-generating composition 2.

A nonwoven fabric 3 having a multiplicity of pores (Oji Kinocloth; manufactured by Oji Paper Co., Ltd.) (22 cm×20 cm) and a comparatively dense nonwoven fabric 4a (Elleair tissue; manufactured by Daio Paper Corp.) (22 cm×20 cm) were bonded with an ethylene-vinyl acetate emulsion adhesive. Then, the aforesaid steam-generating composition 2 was uniformly scattered with a nitrogen flow over nonwoven fabric 3 having a plurality of pores, an ethylene vinyl acetate copolymer resin powder was scattered from the upper surface, and vertical vibrations were applied to the nonwoven fabric to retain the scattered materials in the pores of the nonwoven fabric. Nonwoven fabric 4b was then placed on the upper surface of nonwoven fabric 3, and the obtained laminated material was compressed and heated at a temperature of 200° C. under a pressure of 100 kg/cm to obtain a sheet-like steam generation portion 1A having a thickness of 1.5 mm.

Steam generation portion 1A was cut to a size of 10×8 cm and inserted in a bag having one surface thereof composed of a gas-permeable sheet 8 (Breathlon; manufactured by Nitto Denko Co., Ltd.) and the other surface composed of a moisture-permeable sheet 5a (SWP; manufactured by Mitsui Petrochemical Industries Co., Ltd.) A nonwoven fabric (Syntex V305; manufactured by Mitsui Petrochemical Industries Co., Ltd.) was laminated as a moisture-permeable sheet 5b on the bag surface at the side of the moisture-permeable sheet 5a.

An adhesive composition of the recipe shown in Table 1 was prepared.

TABLE 1

| Recipe of adhesive composition | (units: wt. %) |
|---|---|
| Indometacin | 0.375 |
| L-menthol | 1 |
| Crotamiton | 3 |
| Sodium polyacrylate | 6 |
| Polyacrylic acid | 2.5 |
| Glycerin | 25 |
| Isopropyl myristate | 2 |
| Squalane | 4 |
| Aluminum hydroxide gel | 0.2 |
| Soft amorphous silica | 2 |
| Purified water | Balance |

This adhesive composition was uniformly coated on a PET film to form an adhesive layer that was then covered with a moisture-impermeable sheet 6 (Nitotack; manufactured by Nitto Denko Co., Ltd.) to obtain a laminated sheet (10 cm×14 cm) composed of adhesive layer 7 and moisture-impermeable sheet 6. Holes with a diameter of 0.5 cm were formed therein at a ratio of 6 holes/(10 cm×14 cm) as openings H, and the laminated sheet was laid, by the moisture-impermeable sheet 6 thereof, on the moisture-permeable sheet 5b located on top of the above-described steam generation portion 1A. Steam generator 10A thus obtained was sealed in a sealing bag 9.

Example 2

The steam generator 10B of the embodiment shown in FIGS. 2A, 2B, and 2C was fabricated in the following manner.

A powder prepared by homogeneously mixing 13 g of iron powder (RKH; manufactured by Dowa Iron Powder Co., Ltd.) and 2 g of active carbon was sprinkled from above on a nonwoven fabric 3 having a plurality of pores (Oji Kinocloth; manufactured by Oji paper Col., Ltd.) (20 cm×20 cm) and subjected to vibrations to disperse and retain the powder in the cloth. Then, 10 wt. % brine was scattered in a nitrogen gas flow and uniformly impregnated by pressing with a roller to obtain a steam generation portion 1B.

Steam generator 10B was obtained by using the aforesaid steam generation portion 1B in place of steam generation portion 1A in the process for the manufacture of a steam generator in Example 1.

Example 3

Steam generator 10C shown in FIGS. 3A and 3B was fabricated in the following manner.

First, six steam generation portions 1A with a size of the bottom surface (nonwoven fabric 4b) of 3 cm×3 cm were fabricated in the same manner as in Example 1 and arranged in a row on a moisture-permeable sheet 5b (10 cm×14 cm). Steam generator 10C was obtained by placing a laminate composed of adhesive layer 7 and moisture-impermeable sheet 6 sheet identical to those of Example 1 and having the holes with a diameter of 1.0 cm formed therein at a ratio of 6 holes/(10 cm×14 cm) on moisture-permeable sheet 5b.

Example 4

Steam generator 10D shown in FIGS. 4A and 4B was fabricated.

The fabrication was conducted in the same manner as in Example 1, except that a sheet having a size of 10 cm×10 cm and openings H with a diameter of 1 cm arranged at a ratio of 4 openings/(10 cm×10 cm) was used in place of the laminated sheet of adhesive layer 7 and moisture-impermeable sheet 6.

Comparative Example 1

A steam generator of comparative example was obtained by inserting the steam-generating composition identical to that of Example 1 in a bag (10 cm×14 cm) having one surface thereof composed of gas-permeable sheet 8 (Breathlon; manufactured by Nitto Denko Co., Ltd.) and the other surface composed of moisture-permeable sheet 5a (SWP; manufactured by Mitsui Petrochemical Industries Co., Ltd.) (Breathlon; manufactured by Nitto Denko Co., Ltd.), laying the moisture-permeable sheet 5b on the surface of moisture-permeable sheet 5a of the bag, and then laying thereon a laminated sheet (10 cm×14 cm) composed of adhesive layer 7 and moisture-impermeable sheet 6 identical to those of Example 1 and provided with holes with a diameter of 1.0 cm at a ratio of 4 holes/(10 cm×14 cm).

(Evaluation 1)

The steam generators obtained in Example 1 and Comparative Example 1 were attached to the waist of several people and removed at a time shown in Table 2 and Table 3 after the attachment. The amount of steam discharged through each opening H (Ha, Hb, Hc, Hd, He, Hf) at the adhesive layer side was measured with the transepidermal water evaporation measurement apparatus. The results are shown in Table 2 and Table 3.

TABLE 2

Example 1

(units: $g/m^2$ hr)

| Opening | Time after attachment (min.) | | | | |
|---|---|---|---|---|---|
|  | 5 | 15 | 30 | 60 | 90 |
| Ha | 58 | 110 | 105 | 100 | 88 |
| Hb | 65 | 105 | 100 | 98 | 92 |
| Hc | 70 | 112 | 102 | 98 | 87 |

TABLE 2-continued

Example 1

(units: $g/m^2$ hr)

| Opening | Time after attachment (min.) | | | | |
|---|---|---|---|---|---|
|  | 5 | 15 | 30 | 60 | 90 |
| Hd | 70 | 115 | 98 | 105 | 90 |
| He | 62 | 108 | 104 | 95 | 88 |
| Hf | 60 | 100 | 110 | 102 | 85 |

TABLE 3

Comparative Example 1

(units: $g/m^2$ hr)

| Opening | Time after attachment (min.) | | | | |
|---|---|---|---|---|---|
|  | 5 | 15 | 30 | 60 | 90 |
| Ha | 60 | 78 | 31 | 10≧ | 10≧ |
| Hb | 70 | 55 | 25 | 10≧ | 10≧ |
| Hc | 68 | 34 | 12 | 10≧ | 10≧ |
| Hd | 75 | 120 | 150 | 50 | 32 |
| He | 78 | 154 | 175 | 61 | 48 |
| Hf | 80 | 190 | 168 | 35 | 25 |

The results shown in Tables 2 and 3 demonstrate that in the steam generator of Comparative Example 1, the steam-generating composition was displaced in the course of attachment and, therefore, the steam generation portion was also displaced, whereas in the steam generator of Example 1, the steam was discharged uniformly from all of the openings.

(Evaluation 2)

Example 1 and Comparative Example 1 were repeated as described above, except that the adhesive compositions used in the examples were prepared by removing indometacin and crotamiton from the adhesive composition recipe shown in Table 1, and steam generators of Example 1b and Comparative Example 1b were obtained.

Those steam generators were attached to the waist of several people (a panel of 18 people), and a questionnaire study was conducted with respect to a general feeling in usage, temperature, and unevenness in temperature. The results shown in Table 4 were obtained. Table 4 demonstrates that the steam generator of Example, in which the steam was discharged uniformly from all of the openings, was superior to the steam generator of comparative example is terms of general feeling in usage.

TABLE 4

| General feeling in usage | |
|---|---|
| Example 1b: | good 89%, no opinion 11%, poor 0% |
| Comparative Example 1b: | good 34%, no opinion 22%, poor 44% |
| Temperature | |
| Example 1b: | good 83%, no opinion 11%, poor 6% |
| Comparative Example 1b: | good 39%, no opinion 39%, poor 22% |
| Unevenness in Temperature | |
| Example 1b: | unevenness in temperature was felt 0%, no opinion 22%, unevenness in temperature was not felt 78% |
| Comparative Example 1b: | unevenness in temperature was felt 56%, no opinion 33%, unevenness in temperature was not felt 11%. |

In accordance with the present invention, safe steam similar to that from a steamed towel can be supplied continuously and without displacement to the skin or mucosa by using a simple structure and the utilization feeling is improved. Furthermore, with an embodiment in which a cosmetic or pharmaceutical component is incorporated in the adhesive layer, the effect of heat and moisture of the steam can greatly improve the utilization efficiency of the cosmetic or pharmaceutical component.

The entire disclosure of the spacification, claims, summary and drawings of Japanese Patent Application No. 2000-252326 is hereby incorporated by reference.

What is claimed is:

1. A steam generator comprising: a steam generation portion comprising a steam-generating composition and pulp fiber as a support so as to inhibit movement of the steam generating composition, the steam-generating composition including a metal powder, activated carbon and a salt to be reacted with water and adapted to discharge steam as the metal powder is oxidized; and an adhesive layer provided on a surface of the steam generator adapted to be applied to at least one of skin or mucosa of a user of the steam generator, wherein the steam-generating composition is disposed in pore-like structures of a paper sheet and the adhesive layer includes at least one opening through which the steam or water vapor is discharged from the steam-generating composition, wherein the adhesive layer includes at least one of a cosmetic and a pharmaceutical component that includes a peeling agent, and the peeling agent includes at least a protease.

2. The steam generator according to claim 1, wherein the adhesive layer comprises a water soluble substrate.

3. The steam generator according to claim 1, further comprising a moisture impermeable layer provided on an outer surface of the steam generation portion.

4. The steam generator according to claim 1, wherein the adhesive layer covers approximately 50% to approximately 99.9% of a surface to which the steam generator is applied.

5. The steam generator according to claim 1, further comprising a moisture permeable layer provided on an outer surface of the steam generation portion.

6. The steam generator according to claim 5, wherein the moisture permeable layer includes at least one of a non-woven fabric and a synthetic paper.

7. The steam generator according to claim 1, further comprising a moisture impermeable layer adjacent to the adhesive layer.

8. The steam generator according to claim 7, wherein at least one opening guiding the steam discharged from the steam generation portion is provided in the impermeable layer.

9. The steam generator according to claim 1, wherein the at least one of a cosmetic and a pharmaceutical component further includes at least one of a blood circulation enhancer, a swelling reduction agent, a slimming agent, a painkiller, a moisture retaining agent, a depilating agent, and an autonomic regulating agent.

10. The steam generator according to claim 9, wherein the at least one of a cosmetic and a pharmaceutical component includes a blood circulation enhancer, and the blood circulation enhancer includes at least one of acidic mucopolysaccharides, chamomile, horse chestnut, ginkgo, hamamelis extract, vitamin E, nicotinic acid derivatives, and alkaloid compounds.

11. The steam generator according to claim 9, wherein the at least one of a cosmetic and a pharmaceutical component includes a swelling reduction agent, and the swelling reduction agent includes at least one of horse chestnut, flavone derivatives, naphthalenesulfonic acid derivatives, anthocyanins, vitamin P, calendula officinalis, concholytic acid, silanol, Terminalia, Visnaga, and Majus.

12. The steam generator according to claim 9, wherein of a cosmetic and a pharmaceutical component includes a slimming agent, and the slimming agent includes at least one of aminophylline, tea extract, caffeine, xanthine derivatives, inositol, dextransulfuric acid derivatives, horse chestnut, aescin, anthocyanadin, organoiodine compounds, *Hypericum erectum, Spiraea japonica, Equisetum arvense, Rosmarinus officinalis*, gingsen, *Hedera rhombea, thomucase*, and *hyaluronidase*.

13. The steam generator according to claim 9, wherein the at least one of a cosmetic and a pharmaceutical includes a painkiller, and the painkiller includes at least one of indometacin, diclofenac, dl-camphor, flurbiprofen, ketoprofen, cayenne pepper extract, piroxicam, felbinac, methyl salycilate, and glycol salicylate.

14. The steam generator according to claim 9, wherein the at least one of a cosmetic and a pharmaceutical agent includes a moisture retaining agent, and the moisture retaining agent includes a polyol.

15. The steam generator according to claim 9, wherein the at least one of a cosmetic and a pharmaceutical component includes a depilating agent, and the depilating agent includes calcium thioglycolate.

16. The steam generator according to claim 9, wherein the at least one of a cosmetic and a pharmaceutical component includes an automatic regulating agent, and the autonomic regulating agent includes γ-oryzanol.

* * * * *